United States Patent
Shu et al.

(10) Patent No.: US 9,446,067 B2
(45) Date of Patent: Sep. 20, 2016

(54) MERCAPTO-MODIFIED BIOCOMPATIBLE MACROMOLECULE DERIVATIVES WITH LOW DEGREE OF MERCAPTO-MODIFICATION AND THE CROSS-LINKED MATERIALS AND USES THEREOF

(75) Inventors: Xiaozheng Shu, Jiangsu (CN); Weiping Zhong, Jiangsu (CN); Yunyun Wang, Jiangsu (CN); Meixia Yu, Jiangsu (CN)

(73) Assignee: Bioregen Biomedical (Changzhou) Co. Ltd., Jiangsu (CN)

( * ) Notice: Subject to any disclaimer, the term of this patent is extended or adjusted under 35 U.S.C. 154(b) by 483 days.

(21) Appl. No.: 13/821,666

(22) PCT Filed: Aug. 4, 2011

(86) PCT No.: PCT/CN2011/077985
§ 371 (c)(1),
(2), (4) Date: Sep. 6, 2013

(87) PCT Pub. No.: WO2012/031515
PCT Pub. Date: Mar. 15, 2012

(65) Prior Publication Data
US 2013/0338099 A1    Dec. 19, 2013

(30) Foreign Application Priority Data
Sep. 9, 2010  (CN) .......................... 2010 1 0277374

(51) Int. Cl.
| | | |
|---|---|---|
| A61K 31/737 | (2006.01) | |
| A61K 31/728 | (2006.01) | |
| A61K 31/573 | (2006.01) | |
| C08B 37/00 | (2006.01) | |
| C08B 37/08 | (2006.01) | |
| C08J 3/075 | (2006.01) | |
| C08F 8/34 | (2006.01) | |
| A61L 31/04 | (2006.01) | |
| A61K 45/06 | (2006.01) | |

(52) U.S. Cl.
CPC ........... *A61K 31/737* (2013.01); *A61K 31/573* (2013.01); *A61K 31/728* (2013.01); *A61K 45/06* (2013.01); *A61L 31/04* (2013.01); *C08B 37/0069* (2013.01); *C08B 37/0072* (2013.01); *C08F 8/34* (2013.01); *C08J 3/075* (2013.01); *C08J 2301/00* (2013.01)

(58) Field of Classification Search
CPC .................................................. A61K 31/737
USPC .................................. 536/118, 122; 514/54
See application file for complete search history.

(56) References Cited

U.S. PATENT DOCUMENTS

| 6,884,788 B2 | 4/2005 | Bulpitt et al. |
| 7,196,180 B2 | 3/2007 | Aeschlimann et al. |
| 8,367,818 B2 * | 2/2013 | Yoshida .................. A23L 1/056 536/55.1 |
| 2010/0204102 A1 * | 8/2010 | Akiyoshi et al. ............... 514/12 |

FOREIGN PATENT DOCUMENTS

| CN | 101200504 A | 6/2008 |
| CN | 101365420 A | 2/2009 |
| CN | 101367884 A | 2/2009 |
| CN | 101511875 A | 8/2009 |
| JP | 2003146890 A * | 5/2003 |
| JP | 2009520723 A | 5/2009 |
| WO | 00/25823 A1 | 5/2000 |
| WO | 02/068383 A2 | 9/2002 |
| WO | 2004/037164 A2 | 5/2004 |
| WO | 2004/046200 A1 | 6/2004 |
| WO | 2005/056608 A1 | 6/2005 |
| WO | 2008/008857 A1 | 1/2008 |
| WO | 2008/071058 A1 | 6/2008 |
| WO | 2008/083542 A1 | 7/2008 |

(Continued)

OTHER PUBLICATIONS

Mihara, et al., Different effects of high molecular weight sodium hyaluronate and NSAID on the progression of the cartilage degeneration in rabbit OA model, OsteoArthritis and Cartilage 15, pp. 543-549, 2007.

(Continued)

*Primary Examiner* — Patrick Lewis
*Assistant Examiner* — Everett White
(74) *Attorney, Agent, or Firm* — MKG, LLC

(57) ABSTRACT

The present invention discloses a mercapto-modified biocompatible macromolecule derivative with a low degree of modification. The mercapto-modified biocompatible macromolecule derivative not only maintains the initial structure, physiological function and biocompatibility as much as possible, but also allows the preparation of the biocompatible macromolecule cross-linked material with a low degree of cross-linking through the effectively chemical cross-linking with the introduced mercapto group. The present invention further discloses a disulfide-bond cross-linked biocompatible macromolecule material with a very low degree of cross-linking. The disulfide-bond cross-linked biocompatible macromolecule material not only maintains the initial structure, physiological function and biocompatibility of the biocompatible macromolecule as much as possible, but also effectively prolongs turn over and reduces the solubility of the biocompatible macromolecule in vivo, better meeting the requirements of various clinical applications. The present invention further relates to the application of the disulfide-bond cross-linked biocompatible macromolecule material in the field of medicine and pharmacy.

6 Claims, 1 Drawing Sheet

(56) References Cited

FOREIGN PATENT DOCUMENTS

| WO | 2009/006780 A1 | 1/2009 |
|---|---|---|
| WO | 2009/132226 A1 | 10/2009 |
| WO | 2009132226 A1 | 10/2009 |
| WO | 2010/043106 A1 | 4/2010 |

OTHER PUBLICATIONS

International Search Report for PCT/CN2011/077985, dated Nov. 17, 2011, pp. 1-4.

International Preliminary Report on Patentability for PCT/CN2011/077985, dated Jun. 4, 2013, pp. 1-7.

K. Kafedjiiski et al., Evaluation of In Vitro Enzymatic Degradation of Various Thiomers and Cross-Linked Thiomers, Drug Development and Industrial Pharmacy, 2007, pp. 199-208.

S. Hahn et al., Injectable hyaluronic acid microhydrogels for controlled release formulation of eryhropoietin, Journal of Biomedical Materials Research Part A, Wiley Periodicals Inc., 2006, pp. 916-924.

A. Bernkop-Schnurch et al., Polymers with Thiol Groups: A New Generation of Mucoadhesive Polymers?, Pharmaceutical Research, vol. 16, No. 6, 1999, pp. 876-881.

X. Zheng Shu et al., Disulfide-crosslinked hyaluronan-gelatin hydrogel films: a covalent mimic of the extracellular matrix for in vitro cell growth, Biomaterials 24, 2003, pp. 3825-3834.

X. Zheng Shu et al., Disulfide Cross-Linked Hysluronan Hydrogels, Biomacromolecules 2002, 3, pp. 1304-1311.

M. Proctor et al., Composition of hyaluronan affects would healing in the rabbit maxillary sinus, American Journal of Rhinology, Mar.-Apr. 2006, vol. 20, No. 2, pp. 206-211.

A. Bernkop-Schnurch, Thiomers: A new generation of mucuoadhesive polymers, Advanced Drug Delivery Reviews 57, 2005, pp. 1569-1582.

Jacob, et al., MeroGel Hyaluronic Acid Sinonasal Implants: Osteogenic Implications, Laryngoscope, 112: pp. 37-42, Jan. 2002.

Shu, et al., Disulfide Cross-Linked Hyaluronan Hydrogels, Biomacromolecules, 3: pp. 1304-1311, 2002.

Gianolio, et al., Synthesis and Evaluation of Hydrolyzable Hyaluronan-Tethered Bupivacaine Delivery Systems, Bioconjugate Chemical, 16: pp. 1512-1518, 2005.

Yamauchi, et al., Films of Collagen Cross-Linked by S—S bonds: Preparation and Characterization, Biomaterials 22: pp. 855-863, 2001.

Nicolas, et al., Denatured Thiolated Collagen, Biomaterials 18: pp. 807-813, 1997.

Sparer, et al., Controlled Release from Glycosaminoglycan Drug Complexes, Chapter 6, pp. 107-119, University Microfilms, 1982.

Wang, et al., Synthesis and Characterization of Novel Bioadhesive Material Thiolated Chitosan, Chemical Journal of Chinese Universities vol. 29, No. 1, pp. 206-211, 2008, English abstract.

Appendix VI, G. Determination of Viscosity, Pharmacopoeia of the PR of China, second part, 2005 edition, pp. A-48-A-50.

Appendix XX, C, Guidelines for the Stability Testing of Drug Substances and Preparations, Pharmacopoeia of China, vol. 2, 2010 edition, pp. A-239-A-242.

Hemadeh, et al., Prevention of peritoneal adhesions by administration of sodium carboxymethyl cellulose and oral vitamin E, Surgery, vol. 114 No. 5, pp. 907-910, Nov. 1993.

Yetkin, et al., Prevention of peritoneal adhesions by intraperitoneal administration of vitamin E and human amniotic membrane, International Journal of Surgery 7: pp. 561-565, 2009.

* cited by examiner

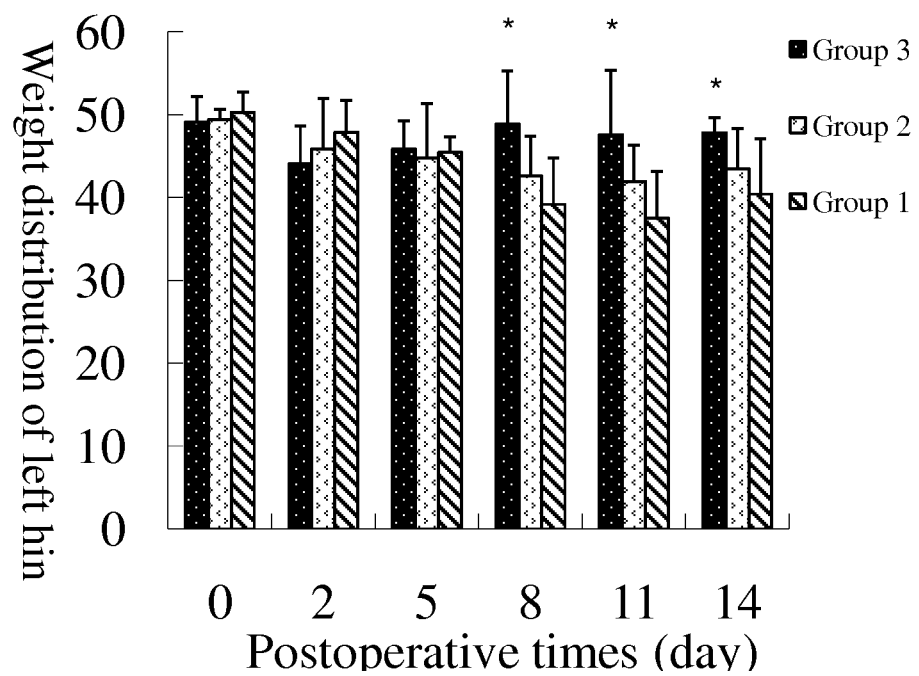

MERCAPTO-MODIFIED BIOCOMPATIBLE MACROMOLECULE DERIVATIVES WITH LOW DEGREE OF MERCAPTO-MODIFICATION AND THE CROSS-LINKED MATERIALS AND USES THEREOF

TECHNICAL FIELD

The present invention relates to a biocompatible macromolecule derivative with a low degree of modification, and particularly to a mercapto-modified biocompatible macromolecule derivative with a low degree of mercapto-modification; the present invention further relates to a disulfide-bond cross-linked biocompatible macromolecule material with a low degree of cross-linking, and in addition further to the use of this cross-linked material in the field of medicine.

BACKGROUND ART

Biocompatible macromolecules have many important physiological functions, such as the significant effects of hyaluronic acid in visco-supplement treatment of osteoarthritis, wound healing promotion etc. However, the biocompatible macromolecules are usually turned over very quickly in vivo or easily dissolved in the body fluid, which largely limits their uses in many medical applications. For example, the course of visco-supplement treatment of hyaluronic acid for osteoarthritis is a knee injection every week for five consecutive weeks, which is inconvenient for patients and medical workers and also increases the risk of infection. The chemical modification, cross-linking or crosslinking after modification is the effective method for biocompatible macromolecules to prolong their turn over and reduce their solubility in vivo, which significantly expands their applications in clinical medicine. For example, as for the visco-supplement treatment of osteoarthritis, the efficacy of one knee injection with the cross-linked sodium hyaluronate is equal to five knee injections with the non-cross-linked sodium hyaluronate; besides, the cross-linked hyaluronic acid has also been widely used for cosmetic purpose such as dermal fillers.

Although the application of the biocompatible macromolecules in the clinical medicine has greatly been expanded through their chemical modification and/or cross-linking, there are still conflicts between theory and practical processes. On one hand, to prolong their turn over and reduce their solubility in vivo the biocompatible macromolecules should be chemical modified/cross-linked to a certain degree. Therefore all those chemically modified and/or cross-linked biocompatible macromolecule derivatives or cross-linked materials, which is widely applied in the clinical medicine currently, have a very high or relatively high degree of modification or cross-linking, such as the highly esterified derivative (up to 100% esterification) of sodium hyaluronate (HYAFF, Fidia, Italy). On the other hand, the chemical structure of the biocompatible macromolecules is changed due to the chemical modification and/or cross-linking, which affects and reduces their physiological function and biocompatible property and even causes certain side effects. For example, the study results reported by Jacob et al showed that MeroGel® (based on the highly modified HYAFF) caused inflammatory reaction and ossification reaction (Jacob et al., Laryngoscope 112: 37-42, 2002).

However, most of the current research has focused on improving the degree of modification and/or cross-linking to prolong turn over and reduce solubility of the biocompatible macromolecule in vivo. In our opinion, the highly modified and/or cross-linked biocompatible macromolecule cannot better meet the requirements of the clinical applications in a considerable number of cases, and may even cause such side effects as an inflammatory reaction etc. Therefore, the chemical modification and/or cross-linking of the biocompatible macromolecule must be balanced between the following two factors: reducing the degree of chemical modification and/or cross-linking as far as possible so as to maintain initial structure, physiological function and biocompatibility, and meanwhile appropriately prolonging turn over and reducing solubility in vivo through chemical modification and/or cross-linking so as to meet the requirements of the clinical applications. However, it is a technical problem to balance the chemical modification and/or cross-linking of the biocompatible macromolecule between the above two factors.

The mercapto-modification and disulfide-bond cross-linking of the biocompatible macromolecule is a new method of chemical modification and cross-linking, and has many advantages and thus many important potential uses in the clinical medicine. For example, the mercapto-modified biocompatible macromolecule derivatives have been used in chemical activity modification of various small molecular drugs and polypeptide protein drugs, etc., and the cross-linked materials prepared based on these mercapto-modified biocompatible macromolecule derivatives can be used as a cell growth matrix, a wound healing and regeneration matrix, a drug sustained-release carrier, a wound dressing, an in situ embedding cell matrix, etc. (Bernkop-Schnurch, WO2000/025823; Shu et al., Biomacromolecules, 3: 1304, 2002; Bulpitt et al., WO2002/068383; Prestwich et al., WO2004/037164; Prestwich et al., WO2005/056608; Prestwich et al., WO2008/008857; Song, WO2008/071058; Song, WO2008/083542; and Gonzalez et al., WO2009/132226). In general, it was deemed that a higher degree of mercapto-modification was needed for the preparation of the subsequent cross-linked material of the mercapto-modified biocompatible macromolecule derivative, and therefore in the above disclosed reference both the degree of mercapto-modification and/or the degree of cross-linking of the biocompatible macromolecule are very high, such as the Shu et al's report wherein 26.8%-66.8% of the groups were modified and cross-linked (Shu et al., Biomacromolecules, 3: 1304, 2002).

DESCRIPTION OF DRAWINGS

FIG. 1 is a schematic diagram of the experimental results of Example 12 of the present invention (i.e. a weight distribution diagram of a left hindfoot).

SUMMARY

One aspect is related to a mercapto-modified biocompatible macromolecule derivative with a low degree of mercapto-modification, the mercapto-modified biocompatible macromolecule derivative contains at least three mercapto groups in its side chain, and have a degree of mercapto-modification≤4.5%; the mercapto-modified biocompatible macromolecule derivative refers to a derivative obtained by chemically introducing the mercapto group into the side-chain group of the biocompatible macromolecule; the degree of mercapto-modification refers to a percentage of the amount of the introduced mercapto group in the amount of the available side-chain group of the biocompatible macromolecule for modification; and the biocompatible macromolecule refers to a macromolecule having good biocompatibility, including polysaccharides, proteins, and synthetic macromolecules.

Another aspect is directed to a disulfide-bond cross-linked biocompatible macromolecule materials made from one or more of the mercapto-modified biocompatible macromolecule derivatives with a low degree of mercapto-modification.

A further aspect is directed to use characterized in that the use in the field of medicine includes a use in preparation of a postoperative adhesion prevention formulation, a use in preparation of an osteoarthritis visco-supplement treatment formulation, and a use as a sustained-release carrier of active therapeutic substances.

The aforementioned aspects and others are described in more detail below.

DETAILED DESCRIPTION

A technical problem to be solved by the present invention is to provide a kind of mercapto-modified biocompatible macromolecule derivatives with a low degree of mercapto-modification. These mercapto-modified biocompatible macromolecule derivatives maintains the initial structure, physiological function and biocompatibility of the original biocompatible macromolecule as much as possible, but also allows the preparation of the biocompatible macromolecule cross-linked material with a low degree of cross-linking through the effectively chemical cross-linking of the introduced mercapto group.

Another technical problem to be solved by the present invention is to provide a disulfide-bond cross-linked biocompatible macromolecule material with a very low degree of disulfide-bond cross-linking. The material of the invention not only have the initial structure, physiological function and biocompatibility of the original biocompatible macromolecule as much as possible, but also prolong their turn over and reduce their solubility in vivo, better meeting the requirements of various medicine applications. Besides, the disulfide-bond cross-linked biocompatible macromolecule material, allowing its cross-linking process to be completed in an injectable container, is injectable, convenient to use, free of impurities, biocompatible, and free of toxic side effects, thus having very wide application prospects in the field of medicine.

Still another technical problem to be solved by the present invention is to provide a use of the above disulfide-bond cross-linked biocompatible macromolecule material in the field of medicine.

Some of the terms used in the present invention are defined as follows.

The biocompatible macromolecule refers to a macromolecule having good biocompatibility, including polysaccharides, proteins, synthetic macromolecules, etc. Wherein the polysaccharides include chondroitin sulfate, dermatan, heparin, heparan, alginic acid, hyaluronic acid, dermatan sulfate, pectin, carboxymethyl cellulose, chitosan, carboxymethyl chitosan, etc., as well as the salts (e.g. sodium salts and potassium salts) and derivatives thereof; the synthetic macromolecules include polyacrylic acid, polyaspartic acid, polytartaric acid, polyglutamic acid, polyfumaric acid, etc., as well as the salts (e.g. sodium salts and potassium salts) and derivatives thereof; the proteins include collagen, alkaline gelatin, acidic gelatin, elastin, core protein, polysaccharide laminin, fibronectin, etc., as well as the salts (e.g. sodium salts and potassium salts) and derivatives thereof. The biocompatible macromolecule is preferably chondroitin sulfate, heparin, heparan, alginic acid, hyaluronic acid, polyaspartic acid, polyglutamic acid, chitosan, carboxymethyl chitosan, alkaline gelatin and acidic gelatin, as well as the salts (e.g. sodium salts and potassium salts) and derivatives thereof, and more preferably chondroitin sulfate and hyaluronic acid, as well as the salts (e.g. sodium salts and potassium salts) and derivatives thereof.

The mercapto-modified biocompatible macromolecule derivative refers to a derivative obtained by chemically introducing a mercapto group into the side-chain group of the biocompatible macromolecule; and the degree of mercapto-modification refers to a percentage of the amount of the introduced mercapto group in the amount of the available side-chain group for modification in the biocompatible macromolecule. For example, when the side-chain carboxyl group of the hyaluronic acid is subjected to mercapto-modification, the degree of mercapto-modification refers to a percentage of the amount of the mercapto group in the total amount of the side-chain carboxyl group of the hyaluronic acid.

Disulfide-bond cross-linking refers to that the mercapto-modified biocompatible macromolecule derivative forms a three-dimensional reticular structure through the disulfide bond; and the degree of disulfide-bond cross-linking refers to a percentage of the amount of the mercapto group of the mercapto-modified biocompatible macromolecule derivative forming the disulfide bond in the amount of the available side-chain group for modification in the biocompatible macromolecule.

Hydrogel refers to a composite containing a great deal of water with three-dimensional cross-linking network structure, which is between liquid and solid without fluidity. Gelation refers to a process through which the liquid state with fluidity turns into the gel without fluidity.

Dynamic viscosity refer to the force for per unit area liquid required to move a unit distance at a unit velocity, which has a unit of centipoise (mPa·s) or poise (Pa·s). The dynamic viscosity is an index for assessing viscosity, the smaller the dynamic viscosity, the better the fluidity, and vice versa.

In one aspect, the present invention provides a mercapto-modified biocompatible macromolecule derivative with a low degree of mercapto-modification, which not only maintains the initial structure, physiological function and biocompatibility of the biocompatible macromolecule as much as possible, but also allows preparation of the biocompatible macromolecule cross-linked material with a low degree of cross-linking through the effectively chemical cross-linking with the introduced mercapto group.

In the present invention, the mercapto-modified biocompatible macromolecule derivativewith a low degree of mercapto-modification can usually be prepared by the following methods, which have been described in the patent document WO2009006780. A first method is the amino group (hydrazide)/carbodiimide coupling chemistry of the side-chain carboxyl group. The usual way is as follows: The carboxyl group is activated by carbodiimide to form an intermediate product that is followed by nucleophilic substitution with a disulfide-bond containing diamino or dihydrazide to produce another intermediate product, and finally the disulfide-bond is reduced into a mercapto group to obtain the mercapto-modified biocompatible macromolecule derivative (Shu et al., Biomacromolecules, 3, 1304, 2002; Aeschlimann et al., U.S. Pat. No. 7,196,180B1). A primary amine containing the free mercapto group (or a mercapto-protected primary amine) can also be used instead of the disulfide-bond containing diamino or dihydrazide to obtain the mercapto-modified biocompatible macromolecule derivative or a intermediate product with mercapto protecting group that is deprotected by removing the mercapto protecting group to obtain the mercapto-modified biocompatible macromolecule derivative (Gianolio et al., Bioconjugate Chemistry, 16, 1512, 2005). The above carbodiimide usually refers to 1-ethyl-3-(3-dimethylaminopropyl)carbodiimide hydrochloride. A second method is to make the preparation through a direct reaction of the side-chain carboxyl group with the disulfide-bond containing carbodiimide (such as 2,2'-dithiobis(N-ethyl-(N'-ethylcarbodiimide))), with the prepared mercapto-modified biocompatible macromolecule derivative having the structure of the following formula (III) (Bulpitt et al., U.S. Pat. No. 6,884,788?). A third method is to modify the side-chain amino group, and generally divided into two ways, i.e. direct and indirect modification. The direct modification method refers to introduce mercapto group through the direct modification of the side-chain amino group, such as the mercapto-modification of the collagen amino group by the activated disuccinic bisacyl-cystamine dicarbonyl diimidazole ester (Yamauchi et al., Biomaterials, 22, 855, 2001; Nicolas et al., Biomaterials, 18, 807, 1997). In the third method the indirect mercapto-modification of the amino group is generally divided into two steps. The first step is carboxylation of the amino group, and the second step is mercapto-modification of the carboxyl group by the foregoing first or second methods. A fourth method is modification of the side-chain hydroxyl group. The usual way is that the hydroxyl group is carboxylated in strong basic conditions, and then the carboxyl group is mercapto-modified in accordance with the foregoing first or second methods. For example, the side-chain hydroxyl group of such macromolecules as cellulose, hyaluronic acid, chitin and chitosan can be carboxymethylated, and is then mercapto-modified through the amino group (hydrazide)/carbodiimide chemical reaction.

For the biocompatible macromolecule with one or more kinds of functional group (carboxyl group, amino group and hydroxyl group), the above one or more methods can be adopted for the preparation of the mercapto-modified biocompatible macromolecule derivative with a low degree of mercapto-modification of the present invention.

In the present invention, the mercapto-modified biocompatible macromolecule derivative with a low degree of mercapto-modification is prepared by the foregoing preparation methods, and the present invention can then be carried out through adjustment of such parameters as the feed ratio of the reaction materials, the reaction time and the reaction temperature etc.

In the present invention, purification of the mercapto-modified biocompatible macromolecule derivative with a low degree of mercapto-modification is very important. Residual impurities may not only produce toxic side effects such as inflammation in vivo, but also interfere with the subsequent disulfide-bond cross-linking. In the present invention, the residual impurities can be removed by dialysis and/or precipitation with organic solvent (e.g. ethanol) etc.

In the present invention, the adopted biocompatible macromolecule has a molecular weight in a range of 1,000-10,000,000 usually, preferably 10,000-3,000,000, more preferably 20,000-1,500,000.

In the present invention, most of the initial structure of the biocompatible macromolecule is retained, with a very low degree of mercapto-modification. The mercapto-modified biocompatible macromolecule derivative with a low degree of mercapto-modification of the present invention contains at least three mercapto groups in its side chain, having a degree of mercapto-modification of ≤4.5%, preferably 0.5%-3.0%, more preferably 0.75%-2.5%.

Researchers generally have a technical prejudice to the mercapto-modified biocompatible macromolecule derivative that a higher degree of mercapto-modification is essential for the preparation of the subsequent cross-linked material and meeting the requirements of the clinical applications. For example, Prestwich et al's researches showed that only the biocompatible macromolecule derivative with a higher degree of mercapto-modification could be cross-linked well (Prestwich et al., WO2008/008857). Therefore, researchers generally tend to improve the degree of mercapto-modification of the biocompatible macromolecule. In 1983 Sparer et al. disclosed the derivatives of glycosaminoglycan (hyaluronic acid and chondroitin sulfate)-cysteine methyl ester, wherein the cysteine methyl ester was coupled with the glycosaminoglycan via an amide bond, and 5%-87% of the side-chain carboxyl group of the glycosaminoglycan was modified into a mercapto group (Sparer et al., Chapter 6, Pages 107-119, Controlled Release Delivery System, Edited by Theodore J. Roseman and S. Z. Mansdorf, Marcel Dekker Inc.). In 2005 Gianolio et al. disclosed the hyaluronic acid-cysteamine derivative, wherein the cysteamine was coupled with the side-chain carboxyl group of the hyaluronic acid via an amide bond, and 22% of the side-chain carboxyl group of the hyaluronic acid was modified into the mercapto group (Gianolio et al., Bioconjugate Chemistry, 16: 1512-1518, 2005). In 2008 Yin et al. disclosed the hyaluronic acid-cysteamine derivative, wherein the cysteamine was coupled with the side-chain carboxyl group of the hyaluronic acid via an amide bond, the derivative contained both 10-200 µmol/g mercapto group and 120-500 µmol/g disulfide bond, and the degree of mercapto-modification was 10%-48% calculated based on that the disaccharide repeating unit of the hyaluronic acid had a molecular weight of 400 (i.e. 10%-48% of the side-chain carboxyl group of the hyaluronic acid was mercapto-modified) (Yin et al., CN 101367884). The hyaluronic acid mercapto-modified derivative coupled via the hydrazide bond disclosed by Shu et al. had a degree of mercapto-modification of 26.8%-66.8% (Shu et al., Biomacromolecules, 3: 1304, 2002).

However, when the degree of mercapto-modification is high, the initial structure of the biocompatible macromolecule is modified significantly, which may compromise its physiological function and biocompatibility. For example, Wang et al's research results showed that the chitosan mercapto-modified derivative produced significant cell toxicity at a high degree of mercapto-modification (Wang et al., Chemical Journal of Chinese universities, 29: 206-211, 2008). Our researches also showed that the high degree of mercapto-modification changed the structure of hyaluronic acid, and interfered in the binding with its receptor (e.g. CD44).

In the present invention, the prepared mercapto-modified biocompatible macromolecule derivative having a low degree of mercapto-modification was purified by the above one or more methods, with the residual impurities usually less than 1/1,000 and even 1/10,000 (weight content).

The present invention has the following advantageous effects: The mercapto-modified biocompatible macromolecule derivative with a low degree of mercapto-modification of the present invention has a very low degree of mercapto-modification, not only maintaining the initial structure, physiological function and biocompatibility of the biocompatible macromolecule as much as possible, but also having such features as consuming little raw materials and costing a short reaction time. Furthermore, the mercapto-modified biocompatible macromolecule derivative with a low degree of mercapto-modification of the present invention can be used conveniently in the preparation of the cross-linked materials and meeting the requirements of various clinical applications. Moreover, the present invention also overcomes the foregoing technical prejudice that a high degree of mercapto-modification is essential for preparation of the subsequent cross-linked material of the mercapto-modified biocompatible macromolecule derivative and meeting the requirements of the clinical applications.

In another aspect, the present invention provides a disulfide-bond cross-linked biocompatible macromolecule material with a very low degree of disulfide-bond cross-linking, which not only maintains the initial structure, physiological function and biocompatibility of the biocompatible macromolecule as much as possible, but also prolongs its turnover and reduces solubility in vivo, better meeting the requirements of various clinical applications. The disulfide-bond cross-linked biocompatible macromolecule material of the present invention is usually present in a form of hydrogel, which has water content preferably of more than 95% (w/v, g/ml), and more preferably of more than 98% (w/v, g/ml). The disulfide-bond cross-linked biocompatible macromolecule hydrogel of the present invention can be made into various solid forms such as film and sponge after being dried or freeze-dried.

The disulfide-bond cross-linked biocompatible macromolecule hydrogel of the present invention was made from the mercapto-modified biocompatible macromolecule derivative with a low degree of mercapto-modification of the present invention. A first method of preparation is as follows: The mercapto-modified biocompatible macromolecule derivative with a low degree of mercapto-modification of the present invention is dissolved in water to obtain a solution of a suitable concentration (usually 0.2%-5.0%), which is adjusted to a specific pH value (usually neutral, i.e. a pH value of about 7), and then the mercapto group is oxidized under the action of the oxygen in the air and the dissolved oxygen in the solution to form the disulfide bond gradually, making the solution gradually gelatinated and the dynamic viscosity of the solution gradually increased, finally making the solution lose fluidity to form a three-dimensional cross-linked network structure. An oxidant (e.g. hydrogen peroxide) can further be added into the above solution to accelerate the cross-linking process.

A second method of preparation of the disulfide-bond cross-linked biocompatible macromolecule hydrogel of the present invention is to use the method disclosed by Shu et al. (WO2010043106). In this method, the gelation process can be completed in an injectable container. And the gel has the advantage of allowing injection, convenient use, no impurities, good biocompatibility, no toxic side effects, etc. This method is specifically as follows: The mercapto-modified biocompatible macromolecule derivative with a low degree of mercapto-modification of the present invention is dissolved in water to obtain a solution of a suitable concentration (usually 0.2%-5.0%), which is adjusted to a specific pH value (usually neutral), and then the solution is filled into the injectable container and sealed, with the mercapto group gradually forming the disulfide-bond mainly under the action of oxidation of the dissolved oxygen in the solution, making the solution gradually gelatinated and the dynamic viscosity of the solution gradually increased, finally making the solution lose fluidity to form a three-dimensional network cross-linked structure. An oxidant (e.g. hydrogen peroxide) can further be added into the above solution to accelerate the cross-linking process.

An aseptic process or a terminal sterilization process (e.g. the moist heat sterilization process commonly used in the pharmaceutical industry) can be adopted in the production when the second method of preparation of the disulfide-bond cross-linked biocompatible macromolecule hydrogel of the present invention is adopted, so as to meet different requirements of clinical medicine. The filling production line commonly used in the pharmaceutical industry can be used to realize the large-scale industrialized production, with the hourly output easily amounting to more than 3000 pieces. The filling production line can be selected from a straight line full-automatic syringe prefilling production line or a beehive syringe full-automatic prefilling-and-plugging machine manufactured by the Groninger company, and a presterilized syringe liquid filling machine manufactured by the Bosch company of Germany, etc. The injectable container can be a syringe made of glass or plastics, such as the Hypak SCF presterilization syringe manufactured by BD company, and the syringe can also be replaced by such extrusible containers as a soft plastic bag.

In the disulfide-bond cross-linked biocompatible macromolecule hydrogel of the present invention, the mercapto-modified biocompatible macromolecule derivative having a low degree of mercapto-modification of the present invention is used as the raw material, and the degree of disulfide-bond cross-linking is dependent on the degree of mercapto-modification ($\leq 4.5\%$), therefore the disulfide-bond cross-linked biocompatible macromolecule hydrogel of the present invention also has a very low degree of disulfide-bond cross-linking ($\leq 4.5\%$). Usually more than half of the mercapto groups in the disulfide-bond cross-linked biocompatible macromolecule hydrogel of the present invention are oxidized into the disulfide bond, which results in the formation of the three-dimensional cross-linked network structure, loss of fluidity of the liquid solution, and the very high dynamic viscosity. Compared with the non-crosslinked solution, the dynamic viscosity of the disulfide-bond cross-linked biocompatible macromolecule hydrogel of the present invention is usually increased by more than 50 times, and can even be increased by more than 500 times under optimal conditions. The disulfide-bond cross-linked biocompatible macromolecule hydrogel of the present invention has such characteristics that it has a unique advantage in such important clinical applications as the prevention and control of postoperative adhesion, and the osteoarthritis visco-supplement treatment.

The dynamic viscosity of the disulfide-bond cross-linked biocompatible macromolecule hydrogel of the present invention was measured with a rotation viscometer at a shear rate of not less than 0.25 Hz and a temperature of 25±0.1 according to the second method in Appendix VI G of the Pharmacopoeia of the People's Republic of China (second part, 2005 Edition), and is typically more than 10,000 centipoise (mPa·s), preferably greater than 25,000 centipoise (mPa·s), and more preferably greater than 40,000 centipoise (mPa·s).

The disulfide-bond cross-linked biocompatible macromolecule material of the present invention may contain one or more mercapto-modified biocompatible macromolecule derivatives with a low degree of mercapto-modification of the present invention, as well as one or more other substances. These substances can be polysaccharides, proteins or synthetic macromolecules, such as chondroitin sulfate, heparin, heparan, alginic acid, hyaluronic acid, polyaspartic acid, polyglutamic acid, chitosan, carboxymethyl chitosan, collagen, alkaline glutin and acidic glutin, as well as the salts (e.g. sodium salts and potassium salts) and derivatives thereof, preferably sodium hyaluronate, chondroitin sulfate, heparin sodium, alkaline glutin and acidic glutin, etc., and more preferably sodium hyaluronate, chondroitin sulfate and heparin sodium; these substances can also be active ingredients, including steroids, antibiotics, drugs for the treatment of tumors, and various polypeptide protein drugs such as cortical hormones (of steroids), e.g. beclomethasone, beclomethasone dipropionate, budesonide, dexamethasone, prednisolone, and prednisone; again such as various polypeptide protein drugs, e.g. various growth factors (an alkaline growth factor, an acidic growth factor, a blood vessel growth factor, an ossification growth factor, etc.), and nucleic acids (e.g. RNA). These active ingredients can be dispersed and/or dissolved in a form of solid particles in the disulfide-bond cross-linked biocompatible macromolecule material of the present invention.

In the actual application in the field of medicine, it is required that the disulfide-bond cross-linked biocompatible macromolecule hydrogel should have an appropriate shelf-life, and its properties should be stable. However, the disulfide-bond cross-linked biocompatible macromolecule hydrogel having a high degree of modification is not stable, the hydrogel gradually contracts such that a large amount of water is extruded from the hydrogel with the increase of the storage time, which makes the dynamic viscosity greatly reduced and seriously affects the gel properties, not meeting the needs of practical clinical applications and seriously restricting application of the disulfide-bond cross-linked biocompatible macromolecule hydrogel in the field of medicine. For example, the volume of hydrogel contracts about 30% after the disulfide-bond cross-linked hyaluronic acid hydrogel (having a degree of mercapto-modification of 13.5%) has been stored at room temperature for six months.

The disulfide-bond cross-linked biocompatible macromolecule hydrogel of the present invention was made from the mercapto-modified biocompatible macromolecule derivative with a low degree of mercapto-modification of the present invention, the unexpected technical effects was achieved, and the above problem of instability of the disulfide-bond cross-linked biocompatible macromolecule hydrogel was solved. The six-month accelerated stability tests showed that the disulfide-bond cross-linked biocompatible macromolecule hydrogel of the present invention has good stability, which will further be described with reference to examples.

The present invention has the following advantageous effects: The disulfide-bond cross-linked biocompatible macromolecule material of the present invention, having a very low degree of cross-linking, not only maintains the initial structure, physiological function and biocompatibility of the biocompatible macromolecule as much as possible, but also has the very high dynamic viscosity, effectively prolongs the turn over and reduces the solubility of the biocompatible macromolecule in vivo, better meets the requirements of various clinical applications. The present invention further has the following advantageous technical effect that the disulfide-bond cross-linked biocompatible macromolecule hydrogel of the present invention has good stability.

In other aspect, the present invention further provides the application of the above disulfide-bond cross-linked biocompatible macromolecule material in the field of medicine.

The applications of the disulfide-bond cross-linked biocompatible macromolecule material of the present invention in medicine include the following aspects: it can be used as wound dressing for skin or other wounds to promote wound healing; it can also be used for preventing adhesion, including the fibrous adhesion between tissues or organs after the surgery (e.g. sinusitis surgery); it can also be used in the osteoarthritis visco-supplement treatment as a knee lubricant.

The applications of the disulfide-bond cross-linked biocompatible macromolecule material prepared by the present invention in pharmacy include that it can be used as a sustained-release carrier for various active therapeutic substances to realize sustained release. The active therapeutic substances may be a chemical drug or a biologically active factor, including antiphlogistics, antibiotics, analgesics, anesthetics, wound healing promoters, cell growth promoters or inhibitors, immune stimulants, antiviral drugs, etc.

The present invention has at least the following advantageous effects: The mercapto-modified biocompatible macromolecule derivative with a low degree of mercapto-modification of the present invention has a very low degree of mercapto-modification, not only maintaining the initial structure, physiological function and biocompatibility of the biocompatible macromolecule as much as possible, but also having such features as consuming little raw material and costing a short reaction time. Furthermore, the mercapto-modified biocompatible macromolecule derivative with a low degree of mercapto-modification of the present invention can be used conveniently in preparation of the cross-linked materials and meeting the requirements of various clinical applications. Moreover, the present invention also overcomes the foregoing technical prejudice that a high degree of mercapto-modification is essential for preparation of the subsequent cross-linked material of the mercapto-modified biocompatible macromolecule derivative and to meet the requirements of the clinical applications.

The present invention has at least the following advantageous effects: The disulfide-bond cross-linked biocompatible macromolecule material of the present invention, having a very low degree of cross-linking, not only maintains the initial structure, physiological function and biocompatibility of the biocompatible macromolecule as much as possible, but also has the very high dynamic viscosity, effectively prolongs the turn over and reduces the solubility of the biocompatible macromolecule in vivo, better meets the requirements of various clinical applications. The present invention further also has the following advantageous technical effect that the disulfide-bond cross-linked biocompatible macromolecule hydrogel of the present invention has good stability.

EXAMPLES

The following examples can make those skilled in the art understand the present invention more completely, rather than limit the present invention in any way.

Example 1

Preparation and Characterization of the Mercapto-Modified Hyaluronic Acid Derivative The preparation was made according to the method disclosed by Shu et al. in Biomacromolecules, 3, 1304, 2002. Dithiodipropionic dihydrazide was added to a solution of hyaluronic acid (11.9 g) in distilled water (2 L). The mixture was stirred until dissolved. Then after pH value of the solution was adjusted to 4.75 with 0.1 mol/L hydrochloric acid, a certain amount of 1-ethyl-3-(3-dimethylaminopropyl) carbodiimide hydrochloride (EDCI) (Aldrich, the United States) was added according to Table 1 under electromagnetic stirring. An amount of 0.1 mol/L hydrochloric acid was added continuously into the above solution to keep the solution at pH 4.75. The reaction was terminated by adding 1.0 mol/L sodium hydroxide to adjust the pH value to 7.0. Then 100 g dithiothreitol (Diagnostic Chemical Limited, the United States) and an amount of 1.0 mol/L sodium hydroxide were added with stirring. pH value of the solution was adjusted to 8.5. The reaction was electromagnetic stirred at room temperature for 24 hours. Then 1 mol/L hydrochloric acid was added into the above solution until pH 3.0. The above solution was loaded into a dialysis tube (the molecular-weight cutoff (MWCO) of 3,500, Sigma, the United States), and was dialyzed for 5 days against a great deal of 0.001 mol/L hydrochloric acid and 0.2 mol/L sodium chloride, with the dialysate changed every 8 hours; then the solution was dialyzed again for 3 days against a great deal of 0.001 mol/L hydrochloric acid, with the dialysate changed every 8 hours. Finally the solution in dialysis tube was collected for direct application or freeze-dried to givewhite flocculent solid.

The content of the mercapto group was detected by the modified Ellman method reported by Shu et al. in Biomacromolecules, 3, 1304, 2002 and the degree of mercapto-modification was calculated, or the degree of mercapto-modification was measured by using the hydrogen spectrum nuclear magnetic resonance ($^1$H-NMR) (with $D_2O$ as the solvent) (taking the characteristic methyl group absorption peak of the acetyl group of hyaluronic acid as the internal standard). The degree of mercapto-modification refers to a percentage of the amount of the mercapto group in the total amount of the side-chain carboxyl group of the hyaluronic acid, with the measurement results as follows:

TABLE 1

Degree of mercapto-modification

| | Serial number | | | | | | | | |
|---|---|---|---|---|---|---|---|---|---|
| | 1 | 2 | 3 | 4 | 5 | 6 | 7 | 8 | 9 |
| EDCI feeding amount (g) | 0.2 | 0.3 | 0.4 | 0.6 | 0.8 | 1.0 | 1.2 | 2.4 | 9.6 |
| Degree of mercapto-modification (%) | 0.48 | 1.04 | 1.46 | 2.33 | 3.24 | 4.18 | 4.61 | 10.6 | 37 |

Example 2

Preparation and Characterization of the Mercapto-Modified Chondroitin Sulfate Derivative 1 g chondroitin sulfate (Type c, from the shark cartilage, Sigma, the United States) was dissolved in 100 ml distilled water to give a clear and transparent solution. To the solution 0.6 g dithiodipropionic dihydrazide was added. The mixture was stirred until dissolved. Then pH value of the solution was adjusted to 4.75 with 0.1 mol/L hydrochloric acid, and a certain amount of 2-ethyl-3-(3-dimethylaminepropyl) carbodiimide hydrochloride (EDCI) (Aldrich, the United States) was added according to Table 2 under electromagnetic stirring. An amount of 0.1 mol/L hydrochloric acid continuously was added into the above solution to keep the solution at pH 4.75. The solution was stirred electromagnetically for 2 hours at room temperature. Then 10 g dithiothreitol (Diagnostic Chemical Limited, the United States) and a little of 0.1 mol/L sodium hydroxide was added with stirring. Meanwhile, 0.1 mol/L sodium hydroxide was added continuously to keep the solution at pH 8.5, and the solution was stirring electromagnetically for 4 hours at room temperature. Then 6 mol/L hydrochloric acid was into the above solution until pH 3.0. The above solution was loaded into a dialysis tube (of the MWCO of 2,000, Sigma, the United States), and was dialyzed for 5 days against 2 L solution of hydrochloric acid (0.001 mol/L) and sodium chloride (0.3 mol/L), with the dialysate changed every 8 hours; then the solution was dialyzed again for 3 days against 2 L hydrochloric acid (0.001 mol/L), with the dialysate changed every 8 hours. Finally the solution in dialysis tube was collected for direct application or freeze-dried to give white flocculent solid.

The content of the mercapto group was detected by the modified Ellman method reported by Shu et al. in Biomacromolecules, 3, 1304, 2002 and the degree of mercapto-modification was calculated, or the degree of mercapto-modification was measured by using the hydrogen spectrum nuclear magnetic resonance ($^1$H-NMR) (with $D_2O$ as the solvent) (taking the characteristic methyl group absorption peak of the acetyl group of chondroitin sulfate as the internal standard). The degree of mercapto-modification refers to a percentage of the amount of the mercapto group in the total amount of the side-chain carboxyl group of the chondroitin sulfate, with the measurement results as follows:

TABLE 2

Degree of mercapto-modification

| | Serial number | | | | | | | | |
|---|---|---|---|---|---|---|---|---|---|
| | 1 | 2 | 3 | 4 | 5 | 6 | 7 | 8 | 9 |
| EDCI feeding amount (g) | 0.01 | 0.015 | 0.02 | 0.03 | 0.04 | 0.05 | 0.06 | 0.12 | 0.48 |
| Degree of mercapto-modification (%) | 0.88 | 1.54 | 1.96 | 3.33 | 4.50 | 5.18 | 6.81 | 15.6 | 42.1 |

Example 3

Preparation and Characterization of the Mercapto-Modified Hyaluronic Acid Derivative Sodium salt of Sulfo-N-hydroxy succinimide (Sulfo-NHS), cystamine dihydrochloride (CYS) and 1-ethyl-3-(3-dimethylaminopropyl) carbodiimide hydrochloride (EDCI) was added to a solution of hyaluronic acid (10 g) in distilled water (1 L) respectively according to the amounts in Table 3. The mixture was stirred until dissolved. Then the pH value of the solution was adjusted to 4.5-6.5 with 0.1 mol/L hydrochloric acid under electromagnetic stirring to react for a period of time. An amount of 0.1 mol/L hydrochloric acid continuously was added into the above solution to keep the solution at pH 4.5-6.5. The reaction was terminated by adding 1.0 mol/L sodium hydroxide to adjust the pH value to 8.5. Then 50 g dithiothreitol (Diagnostic Chemical Limited, the United States) and an amount of 1.0 mol/L sodium hydroxide were added with stirring. The pH value of the solution was adjusted to 8.5. The solution was stirred electromagnetically for 24 hours at room temperature. Then 1 mol/L hydrochloric acid was added into the above solution until pH 3.0. The above solution was loaded into a dialysis tube (the MWCO of 3,500, Sigma, the United States), and was dialyzed for 5 days against a great deal of 0.001 mol/L hydrochloric acid and 0.5 mol/L sodium chloride, with the dialysate changed every 8 hours; then the solution was dialyzed again for 3 days against a great deal of 0.001 mol/L hydrochloric acid, with the dialysate changed every 8 hours. Finally the solution in dialysis tube was collected for direct application or freeze-dried to give white flocculent solid.

The content of the mercapto group was detected by the modified Ellman method reported by Shu et al. in Biomacromolecules, 3, 1304, 2002 and the degree of mercapto-modification was calculated, or the degree of mercapto-modification was measured by using the hydrogen spectrum nuclear magnetic resonance ($^1$H-NMR) (with $D_2O$ as the solvent) (taking the characteristic methyl group absorption peak of the acetyl group of hyaluronic acid as the internal standard). The degree of mercapto-modification refers to a percentage of the amount of the mercapto group in the total amount of the side-chain carboxyl group of the hyaluronic acid, with the measurement results as follows:

TABLE 3

| | Degree of mercapto-modification | | | | | | | | |
|---|---|---|---|---|---|---|---|---|---|
| | Serial number | | | | | | | | |
| | 1 | 2 | 3 | 4 | 5 | 6 | 7 | 8 | 9 |
| Sulfo-NHS (g) | 5.43 | 21.62 | 5.43 | 11.62 | 2.72 | 10.86 | 21.62 | 5.43 | 5.43 |
| CYS (g) | 22.6 | 11.3 | 33.9 | 17 | 5.625 | 22.6 | 11.3 | 22.6 | 11.3 |
| EDCI (g) | 4.8 | 9.6 | 4.8 | 2.4 | 2.4 | 1.2 | 1.2 | 2.4 | 0.72 |
| Reaction time (Hour) | 12 | 3 | 1 | 1 | 1 | 1 | 8 | 8 | 8 |
| Degree of mercapto-modification (%) | 13.5 | 4.83 | 1.54 | 0.84 | 0.73 | 0.51 | 2.14 | 3.97 | 1.28 |

Example 4

Preparation of the Disulfide-Bond Cross-Linked Hyaluronic Acid Hydrogel

The two kinds of mercapto-modified hyaluronic acid derivative prepared in Example 1 (having a degree of mercapto-modification of 2.33% and 4.18%, and indicated as Nos. 4 and 6 in Table 1, respectively) were dissolved to give a 10 mg/ml solution, a 15 mg/ml solution and a 20 mg/ml solution, respectively, with the pH values adjusted to 7.4. The above solutions (2 ml) were transferred into 10 ml glass bottles and sealed respectively, and stand at room temperature for one week. Thus the solutions lose their fluidity and form the cross-linked hydrogels, with the water content of the hydrogels (g/ml) respectively being 99%, 98.5% and 98%.

Example 5

Preparation of the Disulfide-Bond Cross-Linked Chondroitin Sulfate Hydrogel

The mercapto-modified chondroitin sulfate derivative prepared in Example 2 (having a degree of mercapto-modification of 4.50%, and indicated as No. 5 in Table 2) was dissolved to give a 50 mg/ml solution and an 80 mg/ml solution, respectively, with the pH values adjusted to 7.4. The above solutions (2 ml) were transferred into 10 ml glass bottles and sealed respectively, and stand at room temperature for one week. Thus the solutions lose their fluidity and form the cross-linked hydrogels, with the water content of the hydrogels (g/ml) respectively being 95% and 92%.

Example 6

Preparation of the Disulfide-Bond Cross-Linked Hyaluronic Acid Hydrogel

The four kinds of mercapto-modified hyaluronic acid derivative prepared in Example 3 (having a degree of mercapto-modification of 1.28%, 1.54%, 2.14% and 3.97%, and indicated as Nos. 3, 7, 8 and 9 in Table 3, respectively) were dissolved to give a 5 mg/ml solution, a 7.5 mg/ml solution and a 10 mg/ml solution, respectively, with the pH values adjusted to 7.4. The above solutions (2 ml) were transferred into 10 ml glass bottles and sealed respectively, and stand at room temperature for 10 days. Thus the solutions lose their fluidity and form the cross-linked hydrogels, with the water content of the hydrogels (g/ml) respectively being 99.5%, 99.25% and 99%.

Example 7

Preparation of the Disulfide-Bond Cross-Linked Hyaluronic Acid Hydrogel

The mercapto-modified hyaluronic acid derivative prepared in Example 3 (having a degree of mercapto-modification of 2.14%, and indicated as No. 7 in Table 3) was dissolved to give a 10 mg/ml solution, and then the hyaluronic acid solution (5 mg/ml) and the chondroitin sulfate solution (10 mg/ml) were added according to a volume ratio of 2:1, respectively, with the pH value adjusted to 7.4. 2 ml of the above solution was transferred into a 10 ml glass bottle and sealed, and stand at room temperature for 10 days. Thus the solution loses its fluidity and forms the cross-linked hydrogel.

Example 8

Measurement of Dynamic Viscosity of the Disulfide-Bond Cross-Linked Hyaluronic Acid Hydrogel The dynamic viscosity of the disulfide-bond cross-linked hyaluronic acid hydrogel prepared in Example 6 was measured with a rotation viscometer at a shear rate of not less than 0.25 Hz and a temperature of 25±0.1 according to the second method in Appendix VI G of volume II, Pharmacopoeia of the People's Republic of China (2005 Edition), with the results as shown in Table 4. The dynamic viscosity of the cross-linked hydrogel was increased by 408-547 times compared to the corresponding unmodified hyaluronic acid solution.

TABLE 4

| Concentration of hyaluronic acid (mg/ml) | Dynamic viscosity (mPa · s) | | | | |
|---|---|---|---|---|---|
| | Degree of mercapto-modification (%) 0 | Degree of mercapto-modification (%) 1.28 | Degree of mercapto-modification (%) 1.54 | Degree of mercapto-modification (%) 2.14 | Degree of mercapto-modification (%) 3.97 |
| 5 | 137 | 75000 | 78000 | 81000 | 88000 |
| 7.5 | 198 | >100000 | >100000 | >100000 | >100000 |
| 10 | 245 | >100000 | >100000 | >100000 | >100000 |

Example 9

Preparation and Stability Test of the Disulfide-Bond Cross-Linked Hyaluronic Acid Hydrogel Hydrogel 1: The mercapto-modified hyaluronic acid derivative prepared in Example 3 (having a degree of mercapto-modification of 13.5%, and indicated as No. 1 in Table 3) was dissolved to give a 10 mg/ml solution, with the pH value adjusted to 7.4. 2 ml of the above solution was transferred into a 10 ml glass bottle and sealed, and stand at room temperature for 10 days. Thus the solution loses its fluidity and forms the cross-linked hydrogel.

Hydrogel 2: The hydrogel prepared in Example 6 (the hyaluronic acid mercapto-modified derivative prepared in Example 3, having a concentration of hyaluronic acid of 10 mg/ml and a degree of mercapto-modification of 1.54%, and indicated as No. 3 in Table 3).

It is thus clear that the degree of mercapto-modification of the raw material of Hydrogel 2 (i.e. 1.54%) is obviously lower than that of the raw material of Hydrogel 1 (i.e. 13.5%), that is, the degree of cross-linking of Hydrogel 2 is obviously lower than that of Hydrogel 1.

Stability test: An accelerated stability test was performed on the hydrogels according to the Guiding Principle of Stability Test of Drug Substances and Drug Product as provided in XIX C of volume II, Chinese Pharmacopoeia 2010 edition, with the temperature kept at 40±2 for 6 months; sampling and measuring the dynamic viscosity and contraction percentage (%) of the hydrogel at the end of 0, 1, 2, 3 and 6 months during the test, with the results as shown in Table 5. For Hydrogel 1 having a high degree of cross-linking, with the accelerated stability tests conducted, the dynamic viscosity declined sharply and the volume of the gel decreased consecutively, the volume of the gel having a decreasing percentage of 10.2%, 35.1%, 39.2% and 41.4% respectively after 1, 2 and 3 and 6 months, with a great deal of water extruded from the gel. While Hydrogel 2 having a low degree of cross-linking of the present invention kept a good stability.

TABLE 5

| | | Stability test results | | | | |
|---|---|---|---|---|---|---|
| | | Time (month) 0 | Time (month) 1 | Time (month) 2 | Time (month) 3 | Time (month) 6 |
| Hydrogel 1 | Dynamic viscosity | >100000 | 8750 | <5000 | <5000 | <5000 |
| Hydrogel 1 | Contraction percentage (%) | 0 | 10.2 | 35.1 | 39.2 | 41.4 |

TABLE 5-continued

| | | Stability test results | | | | |
|---|---|---|---|---|---|---|
| | | Time (month) 0 | Time (month) 1 | Time (month) 2 | Time (month) 3 | Time (month) 6 |
| Hydrogel 2 | Dynamic viscosity | >100000 | >100000 | >100000 | >100000 | >100000 |
| Hydrogel 2 | Contraction percentage (%) | 0 | 0 | 0 | 0 | 0 |

Example 10

The Disulfide-Bond Cross-Linked Hyaluronic Acid Hydrogel Preventing the Sinus Ostium Stenosis after the Sinusitis Surgery 10 male pasteurized New Zealand white rabbits with a weight of 3.5-4.0 kg were anesthetized by intramuscular injection of ketamine (35 mg/kg) and toluolzosin (5 mg/kg). After peeling off external backside of their noses, the rabbits were disinfected with iodine, and then anesthetized with a mixed liquid of 3 ml of 1% lidocaine and 1:100,000 adrenaline. Under aseptic conditions, a 2.5 mm perpendicular incision was made along the midline, and the soft tissues and the periosteum covered on the genyantrum were lifted and separated. The anterior wall of the genyantrum was opened with an electric surgical drill, and broken through between middle wall of the genyantrum and the nasal cavity with a 4 mm spherical cutting drill, thus forming a cylindrical ostium of 4 mm in diameter without mucosa on the edge. 5 rabbits at their both sides of the ostium were filled with the hydrogel prepared in Example 6 (having a concentration of hyaluronic acid of 10 mg/ml, and a degree of mercapto-modification of 1.54%) (the treated group), and the other 5 rabbits at their both sides of the ostium was filled nothing (the control group). Then the periosteum was sutured interruptedly with an absorbable suture, and the skin was sutured with an absorbable suture to seal the genyantrum. No other dressing was used. The animals were fed with normal diet and drinking water after the operation.

The rabbits were killed after two weeks. The healed wound was incised after the killing to expose the sinus cavity. The residue in the sinus cavity was flushed with water and sucked gently with an extractor. The medial wall of the sinus was inspected with a 30-degree nasal endoscope and recorded. Each of the ostium was measured with a ruler of millimeter scale. The ostium was observed and measured by the double-blind method. The ostium in the treated group had a diameter of 2.78±1.17 mm, while the ostium of the control group had a diameter of 0.7±0.52 mm.

The stenosis of the ostium, as an important problem with the sinusitis clinical surgery, will affect the surgical effect, and even cause the sinusitis relapse. The above results indicate that the disulfide-bond cross-linked hyaluronic acid hydrogel having a low degree of cross-linking of the present invention can significantly prevent the ostium from stenosis, and is thus expected to have wide applications in clinics.

Example 11

Application of the Disulfide-Bond Cross-Linked Hyaluronic Acid Hydrogel in the Postoperative Adhesion Prevention The rat cecum model reported by Hemadeh et al. (Surgery 114: 907-10, 1993) and Yetkin et al. (Int J Surg 7: 561-65, 2009) was used. The process is summarized as follows: 32 rats were divided into 3 groups, with the serosa luster of their cecum serosa scraped off using sterile gauze until the surface bleeding; then a drop of anhydrous ethanol was dropped to the bleeding surface to induce further adhesion; Group 1 was a control group without any treatment, Group 2 was treated with 1 ml commercially available hyaluronic acid solution (10 mg/ml), and Group 3 was treated with the hydrogel prepared in Example 6 (having a concentration of hyaluronic acid of 10 mg/ml and a degree of mercapto-modification of 1.54%); finally the surface wound of the rats was sutured. after two weeks the rats were killed and dissected to observe the adhesion status.

The adhesion was evaluated according to the Yetkin et al's adhesion evaluation system (Int J Surg 2009; 7: 561-65), with the results as shown in Table 6. The blank control group (Group 1) had severe adhesion, the commercially available hyaluronic acid therapeutic group (Group 2) had a certain degree of adhesion, and the disulfide-bond cross-linked hyaluronic acid hydrogel of the present invention (Group 3) had the best effects in adhesion prevention.

TABLE 6

| | Adhesion score | | |
|---|---|---|---|
| | Group 1 | Group 2 | Group 3 |
| Adhesion score | 3.4 ± 0.699 | 1.333 ± 1.231 | 0.4 ± 0.699 |

Example 12

Application of the Disulfide-Bond Cross-Linked Hyaluronic Acid Hydrogel in the Osteoarthritis Visco-Supplement Treatment The rabbit arthritis model reported by Mihara et al. (Osteoarthritis and Cartilage 15: 543-549, 2007) was used. The process is briefly described as follows: the rabbit was anesthetized by intramuscular injection of ketamine (35 mg/kg) and toluolzosin (5 mg/kg). The rabbit's left knee joint in the side of kneecap was cut for a 2 cm of incision and then the exposed lateral collateral ligament was cut off; the end of the tendon was cut open to expose the lateral meniscus followed by cutting 3.0-4.0 mm off the middle of the lateral meniscus; the subcutaneous muscle layer and the skin layer were sutured, and about 0.2 ml ampicillin was injected by intramuscular injection in leg.

The rabbits after the partial resection of meniscus were divided into three groups: Group 1 was a control group with physiological saline, and respectively had an intra-articular injection with 0.2 ml physiological saline on 0, 3, 6, 9 and 12 days after the surgery (a total of 5 injections); Group 2 was a group treated with hyaluronic acid, and respectively had an intra-articular injection with 0.2 ml commercially available hyaluronic acid solution (10 mg/ml) on 0, 3, 6, 9 and 12 days after the surgery for treatment (a total of 5 injections); Group 3 was a group treated with the disulfide-bond cross-linked hyaluronic acid hydrogel of the present invention, and had one intra-articular injection with the hydrogel prepared in Example 6 (having a concentration of hyaluronic acid of 10 mg/ml and a degree of mercapto-modification of 1.54%) on 0 day after the surgery (a total of 1 injection); The pain index was measured for postoperative knee on 0, 2, 5, 8, 11 and 14 days after the surgery, with the pain index characterized by the weight distribution of the left hindfoot (Mihara et al., Osteoarthritis and Cartilage 15: 543-549, 2007); the rabbits were killed 15 days later, and the appearance and histological of the postoperative knee damage was evaluated.

The appearance and histological evaluation of the postoperative knee damage indicated that the disulfide-bond cross-linked hyaluronic acid hydrogel of the present invention had an equivalent protective effect on the postoperative knee to the group treated with hyaluronic acid, but was significantly better than the control group with physiological saline. The weight distribution of the left hindfoot indicated that 8, 11 and 14 days after the surgery the treated group (Group 3) of the disulfide-bond cross-linked hyaluronic acid hydrogel of the present invention was significantly better than the physiological saline control group (Group 1) ($p<0.05$); while at all the postoperative observation time points the group treated with hyaluronic acid (Group 2) had no statistically significant difference in effects from the control group with physiological saline (Group 1) ($p>0.05$), and the group (Group 3) treated with the disulfide-bond cross-linked hyaluronic acid hydrogel of the present invention had no statistically significant difference in effects from the group treated with hyaluronic acid (Group 2) ($p>0.05$) (see FIG. 1).

The above results indicate that the disulfide-bond cross-linked hyaluronic acid hydrogel of the present invention has significant effects in the osteoarthritis visco-supplement treatment, with one knee injection able to achieve the equivalent efficacy of five knee injections with the non-cross-linked hyaluronic acid.

Example 13

Preparation and Characterization of the Drug-Containing Disulfide-Bond Cross-Linked Hyaluronic Acid Hydrogel In the preparation process of the disulfide-bond cross-linked hyaluronic acid hydrogel of Example 6 (having a concentration of hyaluronic acid of 10 mg/ml and a degree of mercapto-modification of 3.97%), 0.1-10 mg cortical hormones (e.g. Beclomethasone, Beclomethasone dipropionate, Budesonide, Dexamethasone, Prednisolone, and Prednisone) were added respectively to make the cortical hormones uniformly dispersed in the prepared cross-linked hydrogel.

10 ml phosphate buffer solution was added to 0.2 ml of the above drug-containing cross-linked hydrogel placed into a 15 ml plastic centrifugal tube. Then centrifugal tube was placed in a shaker (37, 100 rpm), and the ultraviolet absorption of the drugs in the supernatant was measured at regular intervals. The measurement wavelengths were as follows:

Beclomethasone 246 nm, Beclomethasone dipropionate 240 nm, Budesonide 248 nm, Dexamethasone 242 nm, Prednisolone 248 nm, and Prednisone 244 nm.

TABLE 7

The cumulative release percentage of the drugs at different time points

| Time (day) | Beclo-methasone | Beclo-methasone dipropionate | Bu-desonide | Dexa-methasone | Pred-nisolone | Pred-nisone |
|---|---|---|---|---|---|---|
| 7 | 68% | <1% | 26% | 41% | 95% | 86% |
| 14 | 87% | <1% | 43% | 63% | 100% | 99% |
| 21 | 94% | <1% | 61% | 75% | 100% | 100% |

It can be seen from the results in the above Table 7 that the disulfide-bond cross-linked hyaluronic acid hydrogel is a good drug sustained-release carrier, having good sustained release effects for the six cortical hormones. Due to the difference in hydrophobicity of the drugs, the release behaviors of the drugs from the hydrogel are very different. The stronger the hydrophobicity of the drug is, the more sustained the release is. For example, the more hydrophilic Prednisolone was released basically completely in 7 days; while for the very hydrophobic Beclomethasone dipropionate, release was rarely detected.

The applications of the disulfide-bond cross-linked biocompatible macromolecule material of the present invention in medicine include the following aspects: it is capable of promoting wound healing, it can be used as wound dressing for skin or other wounds; it can also be used for preventing adhesion, including the fibrous adhesion between tissues or organs after the surgery (e.g. a sinusitis surgery); it can also be used in the osteoarthritis visco-supplement treatment as a knee lubricant.

The applications of the disulfide-bond cross-linked biocompatible macromolecule material prepared by the present invention in pharmacy include that it can be used as a sustained-release carrier for various active therapeutic substances to realize sustained release. The active therapeutic substances may be chemical drugs or biologically active factors, including antiphlogistics, antibiotics, analgesics, anaesthetics, wound healing promotors, cell growth promoters or inhibitors, immune stimulants, antiviral drugs, etc.

What is claimed is:

1. A mercapto-modified biocompatible macromolecule derivative with a low degree of mercapto-modification, the mercapto-modified biocompatible macromolecule derivative comprises:
   at least three mercapto groups in its side chain and having a degree of mercapto-modification of ≤4.5%;
   wherein the mercapto-modified biocompatible macromolecule derivative is obtained by chemically introducing the mercapto group into the side-chain group of the biocompatible macromolecule; and
   further wherein the degree of mercapto-modification is a percentage of an amount of the introduced mercapto group in an amount of available side-chain group of the biocompatible macromolecule for modification; and
   further wherein the biocompatible macromolecule is chondroitin sulfate or hyaluronic acid, or the salts and derivatives thereof.

2. The mercapto-modified biocompatible macromolecule derivative with a low degree of mercapto-modification according to claim 1, wherein the degree of mercapto-modification is 0.5%-3.0%.

3. The mercapto-modified biocompatible macromolecule derivative with a low degree of mercapto-modification according to claim 2, wherein the degree of mercapto-modification is 0.75%-2.5%.

4. The mercapto-modified biocompatible macromolecule derivative with a low degree of mercapto-modification according to claim 1, wherein the biocompatible macromolecule has a molecular weight in a range of 1,000-10,000,000.

5. The mercapto-modified biocompatible macromolecule derivative with a low degree of mercapto-modification according to claim 4, wherein the biocompatible macromolecule has a molecular weight in a range of 10,000-3,000,000.

6. The mercapto-modified biocompatible macromolecule derivative with a low degree of mercapto-modification according to claim 5, wherein the biocompatible macromolecule has a molecular weight in a range of 20,000-1,500,000.

* * * * *